US 8,583,457 B1
(12) United States Patent
Lewis (10) Patent No.: US 8,583,457 B1
(45) Date of Patent: *Nov. 12, 2013

(54) METHOD OF COORDINATING AND DISPLAYING A SHORT NAME OF A DRUG

(71) Applicant: Walgreen Co., Deerfield, IL (US)

(72) Inventor: J. Randolph Lewis, Deer Park, IL (US)

(73) Assignee: Walgreen Co., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/891,925

(22) Filed: May 10, 2013

Related U.S. Application Data

(63) Continuation of application No. 12/168,519, filed on Jul. 7, 2008, now Pat. No. 8,489,430.

(51) Int. Cl.
*G06Q 50/00* (2012.01)
(52) U.S. Cl.
USPC ............... 705/3; 358/1.1; 707/769; 707/790
(58) Field of Classification Search
USPC ................ 358/1.1; 705/3; 707/769, 790
See application file for complete search history.

(56) References Cited

U.S. PATENT DOCUMENTS

| 4,760,528 | A * | 7/1988 | Levin ............................ 715/234 |
| 5,001,654 | A * | 3/1991 | Winiger et al. ................ 715/210 |
| 6,195,665 | B1 * | 2/2001 | Jarett ............................. 715/251 |
| 6,944,832 | B2 * | 9/2005 | Riedl et al. .................... 716/105 |
| 7,475,343 | B1 * | 1/2009 | Mielenhausen ............... 715/261 |
| 8,095,387 | B2 * | 1/2012 | Nicholson et al. ................. 705/3 |
| 2004/0054639 | A1 * | 3/2004 | Muno et al. ...................... 707/1 |
| 2007/0192377 | A1 * | 8/2007 | Gies ............................. 707/200 |

* cited by examiner

*Primary Examiner* — Peter K Hutsinger
(74) *Attorney, Agent, or Firm* — Francis C. Kowalik; Marshall, Gerstein & Borun LLP; Randall G. Rueth (57) ABSTRACT

A system and methods for coordinating and displaying a short name of a drug are disclosed. The short name may be a subset of the prescribed drug's name, it may be an independent name, or it may be a graphical symbol. Short names for multiple drugs of a patient may be related by a common naming convention. Short names may be printed onto a reference card along with an indication corresponding to the drug's dosing regime. Short names may also be printed onto medicament container labels, additional instruction sheets, labels used for stocking and the like. The short name may be selectable and may be stored.

20 Claims, 7 Drawing Sheets

METHOD OF COORDINATING AND DISPLAYING A SHORT NAME OF A DRUG

CROSS-REFERENCE TO RELATED APPLICATIONS

This application is a continuation of U.S. patent application Ser. No. 12/168,519, filed Jul. 7, 2008, the entire disclosure of which is hereby expressly incorporated herein by reference.

BACKGROUND

Prescription drug medicament containers are required by law to be labeled with the name of the drug contained therein, using, for example, the drug's brand name, generic name or chemical name. These drug names may be long, complex and unfamiliar to a patient who is not associated with the medical industry. Industry drug names may not enable drugs to be easily identified, remembered or distinguished.

This problem may be exacerbated if a patient has multiple prescriptions to be taken at varying times of ingestion. Identifying and remembering multiple drugs using the brand, generic or chemical name may be cumbersome and confusing for the patient or a caregiver of the patient. Furthermore, if a caregiver has multiple recipients under his/her care, each having multiple prescriptions, remembering and identifying the multiple prescription drugs may become even more complex. Similarly, if a patient has multiple caregivers, for instance, a home health provider, an adult child, and several physicians and/or nurses, remembering and identifying multiple prescription drugs and communicating drug information among the multiple caregivers may be difficult.

A solution is needed to simplify the naming of prescription drugs to enable easier identification. The solution may also help patients and/or their caregivers to be more accurate about distinguishing between multiple prescribed drugs and remembering to ingest them at the appropriate time.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Methods and a system for coordinating, displaying and printing a short name of a drug are disclosed. A short name may be an easy-to-remember name and/or graphical symbol that represents the drug. A common naming convention across a set of short names for a set of drugs prescribed for a patient may be used. Short names may be unique across the set of drugs prescribed for a patient. A short name may be printed and/or displayed. A short name of a prescribed drug may be displayed and/or printed in conjunction with an indication of a dosing regime for the prescribed drug. A short name, a common naming convention and/or a representation of indications of dosing regimes may be selectable.

DESCRIPTION

Although the following text sets forth a detailed description of numerous different embodiments, it should be understood that the legal scope of the description is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '________' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
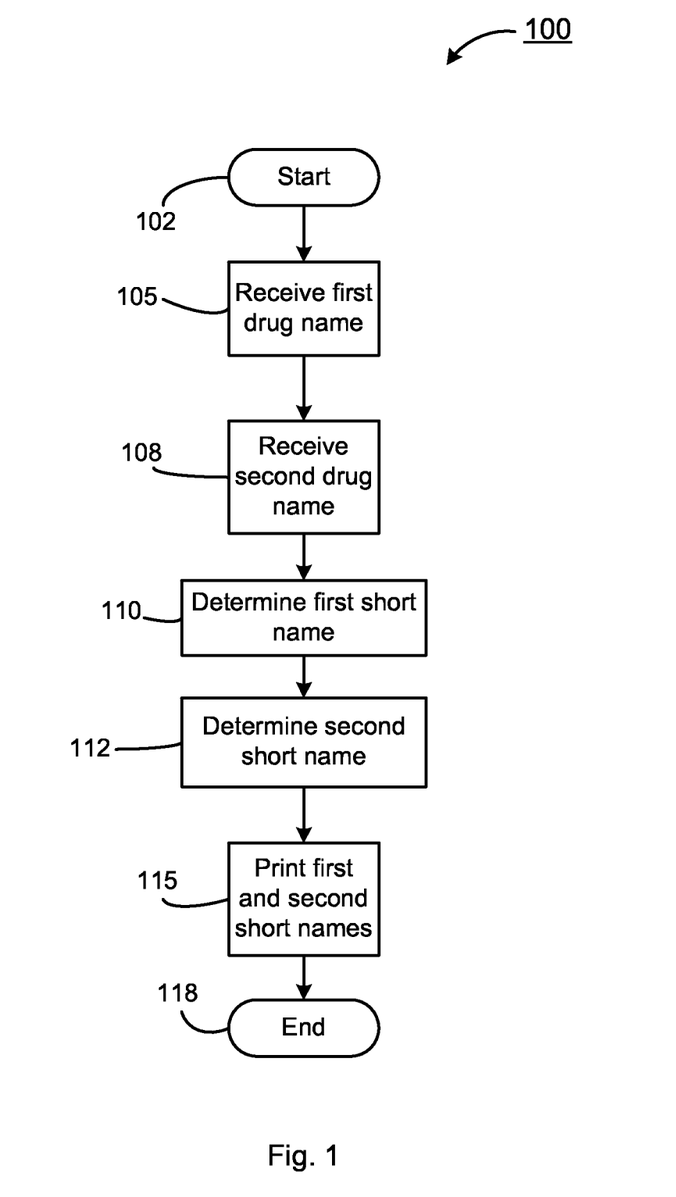
FIG. 1 illustrates an exemplary embodiment of a method of coordinating and displaying a short name for a drug.

FIG. 1 illustrates an exemplary embodiment of a method 100 of coordinating and displaying a short name for a drug. At the start (block 102), a first drug name may be received (block 105). The first drug name may correspond to a first drug of a first prescription for a patient. The first drug name may be a brand name, a generic name, a chemical name or any other type of name that uniquely identifies the first drug. The first drug name may be received (block 105) by, for instance, a pharmaceutical professional receiving a paper prescription from a person at a pharmacy counter. The first drug name may be received (block 105) via a mail or fax order system. The first drug name may be received (block 105) verbally, e.g., if a doctor's office calls in a prescription to a pharmacy. The first drug name may be electronically received (block 105) by a computer at a pharmacy store-front, warehouse, website or other entity that performs the function of filling prescriptions by an email, website order, data transfer, or other electronic means. Any means of receiving a first drug name (block 105) may be possible and may operate in accordance with embodiments of method 100.

At block 108, a second drug name is received. The second drug name may correspond to a second drug of the first prescription for the patient, or the second drug may correspond to a different prescription for the patient. The second drug name, similar to the first drug name, may be a brand name, a generic name, a chemical name or any other type of name that uniquely identifies the second drug. The second drug name may be received (block 108) by using any of the means described for the receiving the first drug name (block 105). The means by which the second drug name is received (block 108) may be the same means or different means by which the first drug name is received (block 105).

At block 110, a first short name corresponding to the first drug name may be determined. The first short name may have a less number of characters than the first drug name. A short name may be determined (block 110) to help the patient, caregiver or other party associated with the patient to more easily identify and remember the drug. For instance, a first short name may be a subset of the first drug name, for instance "AUG" or "MEN" for the antibiotic Augmentin. The first short name may also be independent of the first drug name but simple for a patient to remember, such as "CAT," "JIM," "BLUE," or "HEART." Any easy-to-remember name may be determined as a first short name (block 110). Indeed, a patient or an agent of the patient may be able to select or indicate a desired first short name. An embodiment of a method including selection of short names will be discussed in a later section.

As used herein, an "agent of a patient" may be understood to be one or more persons who are responsible for ensuring that a prescription for a patient is filled. An agent of a patient may be responsible for tasks such as providing the prescription to a pharmacy or other filling entity, providing the filling entity with any information regarding the patient that is needed to fill the prescription, receiving instructions, side effects, warning signs and other such information from the filling entity regarding the prescription, and paying for the filled prescription. An agent of a patient may be, among others, a caregiver, family member, friend, or medical authority. Alternatively, an agent of a patient may be a software program that the patient or party procuring the filled prescription may use or give proxy to, for instance, software used by a patient to order the filling of a prescription with a pharmacy with a website presence.

As used herein, the terms "pharmacy" and "filling entity" may be interchangeably used to mean an entity that is enabled to fill prescriptions. The entity may be, for instance, a storefront pharmacy or a pharmacy that is a department in a larger store. A "pharmacy" or "filling entity" may also be a mail-order, phone-in, fax, website or other entity for filling prescriptions. A "pharmacy" or "filling entity" may even be in a physician's office, clinic or hospital. Any entity enabled to fill prescriptions may be interpreted by the present application to be a "pharmacy" or "filling entity."

As used herein, a "pharmaceutical professional" may be understood to be one or more persons employed by a filling entity or its agents who may be responsible for at least one step in the filling of a prescription, for instance, a pharmacy technician, a pharmacist or other pharmacy employee. A "pharmaceutical professional" may be a medical authority or an agent of a medical authority, such as when a physician's office directly fills prescriptions for its patients. Alternatively or additionally, a "pharmaceutical professional" may also be a software program through which the patient or party procuring the filled prescription may use, for instance, software used by a website pharmacy to fill a prescription using an on-line interface with a patient or agent of a patient.

Continuing with method 100, at block 112, a second short name corresponding to the second drug name may be determined. The second short name may have fewer characters than the second drug name. Any easy-to-remember name may be determined as a second short name (block 112), however, a preferred embodiment may determine the second short name by using a common naming convention that was used to determine the first short name (block 110). For instance, if the first short name was determined to be "AUG" for a first drug Augmentin (block 110), then the second short name may use the common naming convention of the first syllable of the drug name, and determine a second short name of "FLO" for a second drug Flonase (block 112). In another example, if the first short name was determined to be "CAT" (block 110), then the second short name may be determined to be a different animal (block 112), such as "DOG" or "MOUSE." In yet another example, if the first short name is determined to be "BLUE" (block 110), then the second short name may be determined to be a different color (block 112), such as "RED" or "BLACK."

Common naming conventions may be any naming convention that may be related in form or content, such as but not limited to a portion of the drug name, a color, a shape, a graphical symbol or other category. An embodiment of method 100 may allow a patient or an agent of the patient to select a common naming convention and/or short names within the common naming convention, thus enabling customization to a convention that is most easily remembered by the party administering the prescription drugs to the patient. For instance, a common naming convention may correlate to physical colors of the actual pills for the first and second drugs, e.g., "BLUE" and "PINK." Or, a common naming convention may correlate to the dosing regimes, e.g., "WATER" for a first drug to be taken with water and "FOOD" for a second drug to be taken with food. Another example of a common naming convention may correlate to the number of pills to be dosed at the same time, e.g., "TWO" for a first drug that is required to be taken two pills at a time, and "ONE" for a second drug that is required to be taken one pill at a time. Common naming conventions may not be limited to the examples described herein, and may include any naming convention.

A convention used for the common naming convention may be able to be selected, indicated, created and/or updated by the patient, an agent of the patient, a pharmaceutical professional or a system administrator for a system that executes at least a portion of an embodiment of method 100. Additionally, one or more individual short names within a common naming convention may also be able to be selected, indicated, created and/or updated by one or more of the parties. Any selections, indications, creations and/or updates may be stored. A default naming convention and/or default short names may be used if no preference is indicated or stored. An embodiment may have each determined short name unique across the set of short names corresponding to the set of drugs prescribed for a patient, so that the party administering the set of drugs to the patient may easily identify and distinguish between the medications. The set of drugs may correspond to drugs from one or more prescriptions for the patient.

Continuing on with the embodiment of method 100, at block 115, the first and the second short names may be printed. Each of the first and the second short names may be printed (block 115) onto medicament containers or onto labels for medicament containers for the first and the second drugs, respectively, along with other standard medicament container labeling information. By printing the short names (block 115) with the standard labeling information, a key may be provided for translating between a drug name and a short name. The short names may also be printed (block 115) onto a reference card, such as onto a tear-away portion of a drug information sheet that is distributed with a filled prescription, directly onto the information sheet, or onto a stand-alone reference card. The short names may be printed (block 115) onto labels and/or other identification mechanisms for use in stocking the first and the second drugs, such as but not limited to shelf labels, box labels, carton labels, spreadsheets, inventory aids and the like. Persons responsible for stocking the drugs thus may also be provided with easy-to-remember short names by which to reference the drugs. The short names may be also printed (block 115) onto reusable labels for use by patients, their agents, their caregivers, pharmaceutical professionals and others, for instance, for affixing to medical charts in a hospital or for affixing to a pill container partitioned by day-of-the-week. Printing the short names (block 115) may be performed by printing onto any medium that may be used when an easy-to-remember short name for a drug is beneficial.

Finally, at step 118, method 100 may end.

Figure 2:
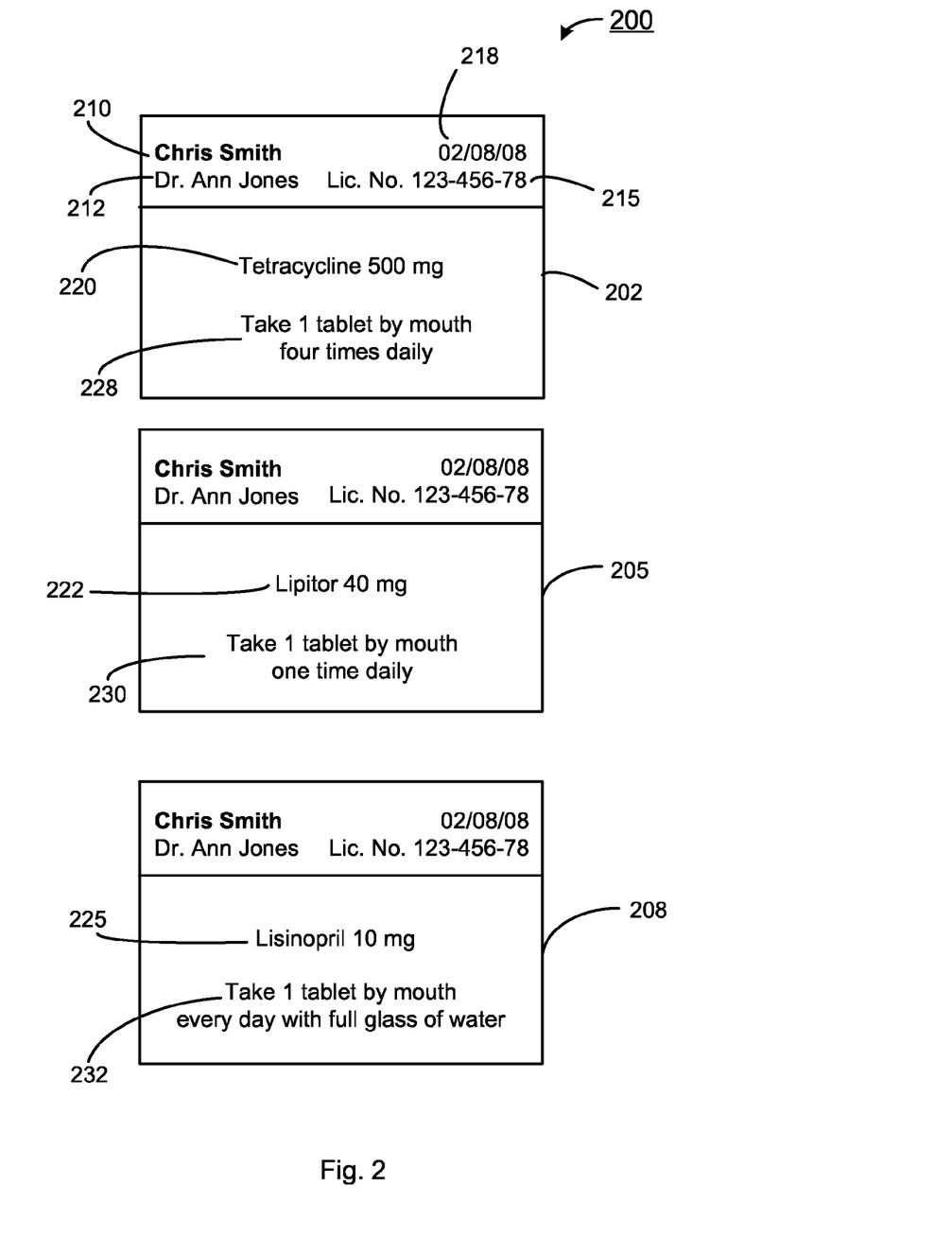
FIG. 2 is an example of a set of prescriptions for a patient.

FIGS. 2, 3*a*, 3*b* and 3*c* illustrate embodiments of an example of a set of prescriptions for a patient Chris Smith and examples of reference cards, each using a different common naming convention for the drugs indicated by the set of prescriptions. FIG. 2 illustrates an example of a set 200 of three prescriptions 202, 205, 208 for patient Chris Smith 210. Each prescription 202, 205, 208 may include standard prescription information such as a patient name 210, an identification of an issuing medical authority 212, a license number of the medical authority 215, and a date of issuance 218. It is understood that the standard prescription information 210, 212, 215, 218 shown in FIG. 2 is only exemplary, and may vary per the regulations of states, provinces, countries and other governmental bodies.

Each prescription 202, 205, 208 may also include the name of a drug 220, 222, 225 along with the dosing regime 228, 230, 232 for the named drug 220, 222, 225. The name of the drug 220, 222, 225 may be a brand name, such as illustrated by "Lipitor" 222, or it may be a generic name, such as illustrated by "Tetracycline" 220 and "Lisinopril" 225. Other formats of drug names may also be used.

Although prescriptions 202, 205, 208 illustrated in FIG. 2 are in paper prescription form, they are not limited to only paper prescription form. Prescriptions 202, 205, 208 may exist in an electronic prescription form. Prescriptions 202, 205, 208 may exist in a verbal form, e.g., when an issuing medical authority calls in a prescription to the pharmacy or filling entity. Different prescriptions may take different forms, for instance, prescription 202 may be in paper form, prescription 205 may be in an electronic form and prescription 208 may be called in by an issuing medical authority. Any known form of a prescription 202, 205, 208 may be used in accordance with the present disclosure.

Figure 3A:
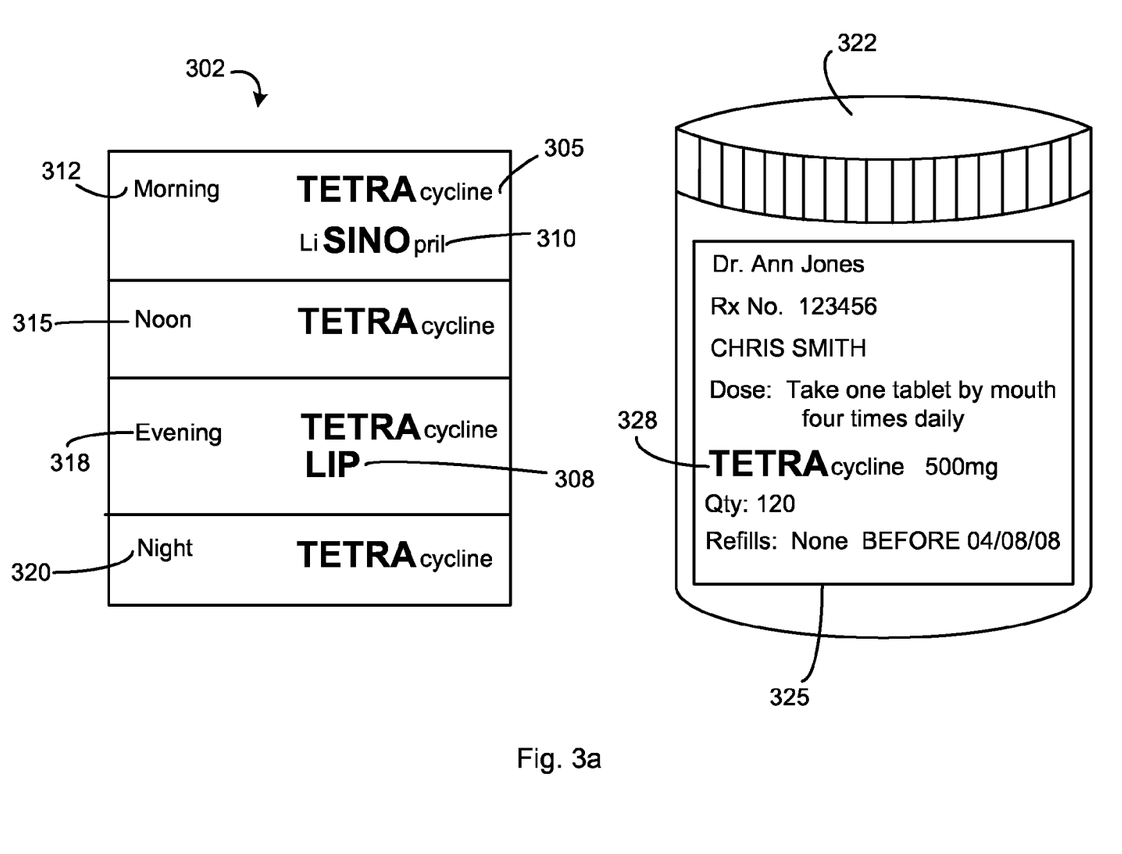
FIG. 3a is an example of a reference card for the prescriptions of FIG. 2 using short names of one common naming convention.

FIG. 3*a* is an example of an embodiment of a reference card 302 for the drugs named in prescriptions 202, 205, 208 of FIG. 2 that uses a common naming convention of a subset of the drug name for the short name. Reference card 302 may be used by patient Chris Smith 210 and/or a caregiver of patient Chris Smith 210 to aid in remembering dosing regimes for Chris Smith's prescribed medications. The drug Tetracycline 220 of prescription 202 may have a short name of TETRA 305, and TETRA 305 may be printed onto reference card 302 using a bold, capitalized font. The remainder of the characters of the drug name Tetracycline 220 may also be printed onto reference card 302, but may use a non-bold, lower-case font to distinguish it from the short name TETRA 305. The drug Lipitor 222 of prescription 205 may have a short name LIP 308, but in this case, the short name LIP 308 may be printed using a bold, capitalized font without the remaining characters of the drug name. Typically, but not necessarily, the short names may be printed using an identical representation or format for each drug. In FIG. 3*a*, however, differing formats for TETRA 305, (including the remainder of the entire drug name) and LIP 308 (excluding the remainder of the entire drug name) are used together on reference card 302 to illustrate possible representation variations. The drug Lisinopril 225 of prescription 208 may have a short name of SINO 310, also a subset of the characters of the drug name, but unlike TETRA 305 and LIP 308, the subset of characters for SINO 310 may be taken from the middle of the drug name.

Short names TETRA 305, LIP 308 and SINO 310 are exemplary. Other embodiments of using a common naming convention of a subset of the characters of a drug name may be possible. For instance, the characters of the short name need not be consecutive, for instance, Tetracycline 200 may have a short name of TetraCycLINe or TCLIN. In another or the same embodiment, the short name need not necessarily be distinguished via capitalization and/or bolding the short name within the drug name—a different color, font, format or other distinguishing printing characteristic may be used to differentiate the short name from the remainder of the drug name. In fact, an embodiment may use a combination of conventions, such as TETRA 305 being capitalized, bolded, and blue, and SINO 310 being capitalized, bolded, and green. Many other embodiments for a common naming convention using a subset of the characters of a drug name may be possible. The common naming convention and/or its printing characteristics may be selectable and updateable by the patient, an agent of the patient, a pharmaceutical professional and/or a system administrator of a system that executes at least a portion of an embodiment of a method of the present disclosure.

An indication of dosing regimes 312, 315, 318, 320 may be printed onto reference card 302. For example, the drug Tetracycline 220 of prescription 202 has a dosing regime of "four times daily" 228. This dosing regime 228 may be indicated on reference card 302 by having short name TETRA 305 appear in the sections labeled "Morning" 312, "Noon" 315, "Evening" 318 and "Night" 320. The drug Lipitor 222 of prescription 205 may have a dosing regime of "one time daily" 230. Lipitor's dosing regime 230 may be indicated on reference card 302 by having short name LIP 308 appear once on reference card 302 in the section labeled "Evening" 318. Similarly, the drug Lisinopril 225 may have its dosing regime 232 reflected on reference card 302 by short name SINO 310 appearing once in the section labeled "Morning" 312. The sections to which each short name may be mapped are exemplary. One of ordinary skill in the art will comprehend that a particular drug's short name may be flexibly mapped, e.g., SINO 310 may not necessarily be mapped to "Morning" 312 to reflect dosing regime 232, but may be mapped to "Noon" 315, "Evening" 318 or "Night" 320. The mapping of dosing regimes 228, 230, 232 to sections of reference card 302 may be automatically performed or may be selectable by the patient, an agent of the patient, a pharmaceutical professional and/or a system administrator. A default mapping may also be available.

In another embodiment, instead of indicating times of ingestion such as "Morning" 312, "Noon" 315, "Evening" 318 and "Night" 320, dosing regimes may be indicated per ingestion instructions (e.g., with water, with food, on an empty stomach). A set of phrases such as "With Water," "With Food," and "On Empty Stomach" may be used. Another embodiment may have dosing regimes indicated by the number of pills to be ingested at a time, e.g., "One," "Two," and "Four." Other dosing regimes and categories of indicating dosing regimes may be used.

An example of a vial 322 containing the medication for the Tetracycline prescription 202 is also illustrated in FIG. 3a. The vial 322 may have a label 325 including standard labeling information, such as but not limited to an identification of the issuing medical professional, identification of the medication 328, an Rx number, a patient name, a dosing regime, and indication of refills, and the like. The label 325 may be preprinted and affixed to vial 322, or the labeling information 325 may be directly printed onto the vial 322. The identification of the vial contents, or prescribed medicine 328, may be represented on label 325 using the same common naming convention as used on its corresponding reference card 302. In this example, similar to the reference card 302, short name "TETRA" may be printed onto label 325 using a bold, capitalized font, and the remainder of the characters of the drug name Tetracycline may be printed using a non-bold, lower-case font to distinguish it from the short name TETRA (reference 328). Although not illustrated, drug vials 322 for Lipitor 222 of prescription 205 and Lisnopril 225 of prescription 208 may have similarly printed labels on their corresponding vials 322. One of ordinary skill in the art will recognize that other types of drug containers may also be used in accordance with the present application, such as blister packs, medicament pouches, and other drug containers.

Figure 3B:
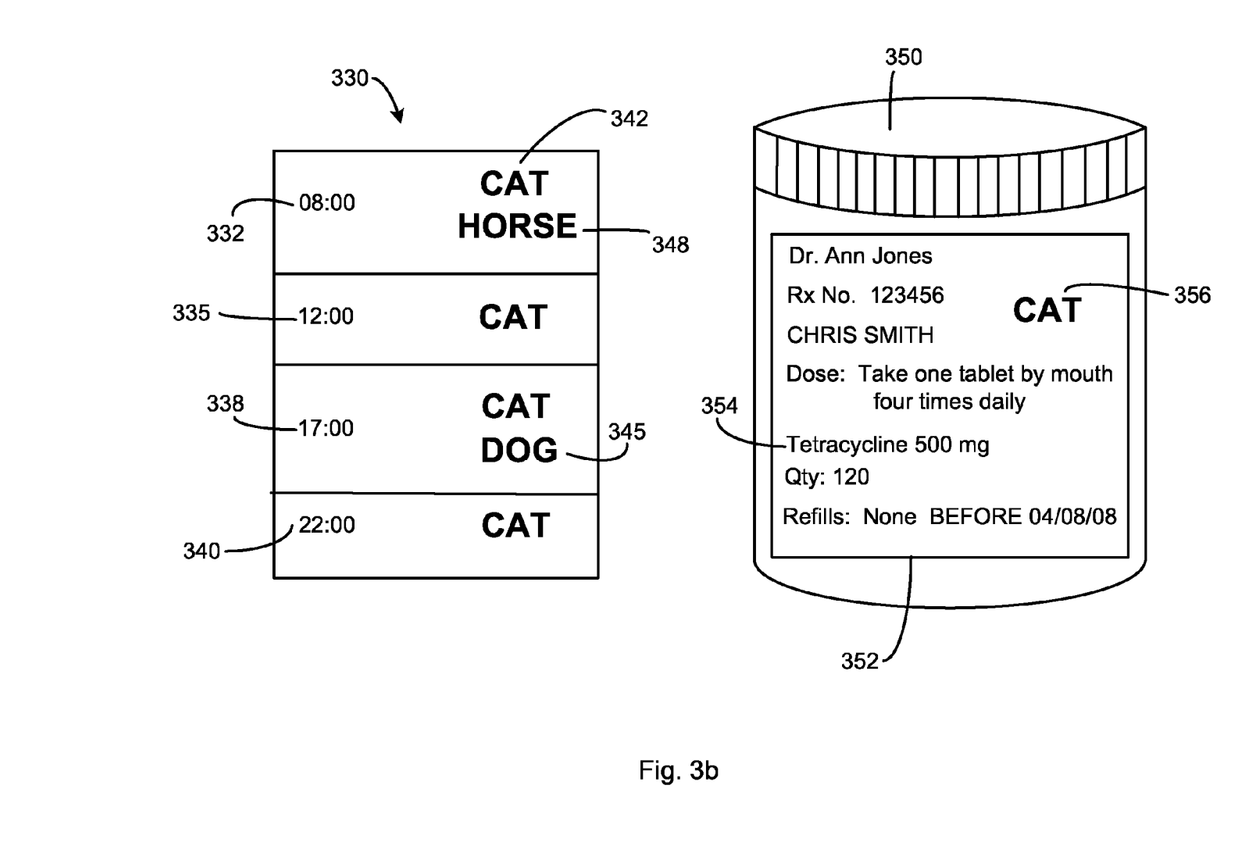
FIG. 3b is an example of another reference card for the prescriptions of FIG. 2 using short names of a different common naming convention.

Turning to FIG. 3b, reference card 330 illustrates an embodiment having the indications of dosing regimes 332, 335, 338, 340 in another different form. In FIG. 3b, the indications of dosing regimes 332, 335, 338, 340 may have a form of a digital 24-hour clock representation. Each indication 332, 335, 338, 340 illustrates a target time for ingesting the prescribed drugs. Indications of dosing regimes 332, 335, 338, 340 may also take other forms or representations, such as but not limited to analog clock representations, graphical symbols, colors, shapes, words, and combinations thereof. Indeed, the indications of dosing regimes 332, 335, 338, 340 may be able to be selected, indicated, created and/or updated by the patient, an agent of the patient, a pharmaceutical professional and/or a system administrator. A default indication for a dosing regime may also be available.

Reference card 330 also illustrates another embodiment of using another common naming convention for the short names corresponding to the drugs of prescriptions 202 205 208 of FIG. 2. In this example, the drug Tetracycline 220 may have the short name CAT 342, the drug Lipitor 22 may have the short name DOG 345, and the drug Lisnopril 225 may have the short name HORSE 348. Each short name 342, 345, 348 may be mapped to be printed in the indicated sections 332, 335, 338, 340 of reference card 330 corresponding to their respective dosing regimes 228, 230, 232. In this example, the indications of the dosing regimes 332, 335, 338, 340 may use a representation of a 24-hour digital clock, but other forms of indications may also be used.

FIG. 3b further illustrates an example of a vial 350 containing the medication for the Tetracycline prescription 202. The vial 350 may have a label 352 including standard labeling information, such as but not limited to an identification of the issuing medical professional, identification of the medication 354, an Rx number, a patient name, a dosing regime, and indication of refills, and the like. The label 352 may be printed and affixed to vial 350, or the labeling information 352 may be directly printed onto the vial 350. The identification of the vial contents or prescribed medicine 354 (in this example Tetracycline 354) may be represented on label 352 using the same common naming convention 356 as used on its corresponding reference card 330. In this example, similar to the reference card 330, short name CAT 356 may be printed onto label 352. Note that vial 350 may have both a standard representation of the medication Tetracycline 354 and its short name 356. Although not illustrated, drug vials 350 for Lipitor 222 of prescription 205 and Lisnopril 225 of prescription 208 may have similarly printed labels on their corresponding vials 350. One of ordinary skill in the art will recognize that other types of drug containers may also be used in accordance with the present application, such as blister packs, medicament pouches, and other drug containers.

Figure 3C:
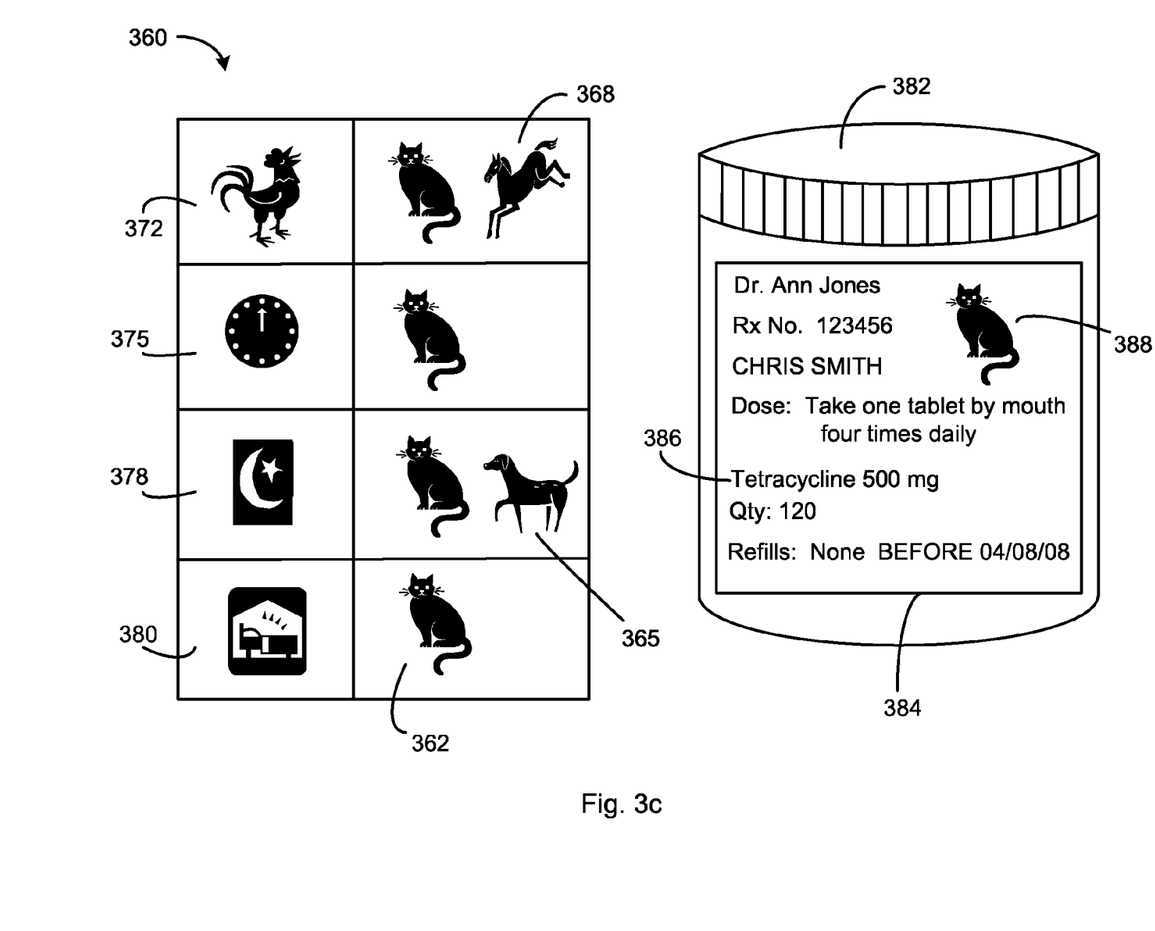
FIG. 3c illustrates another embodiment of a reference card for the prescriptions of FIG. 2 using yet another common naming convention.

FIG. 3c illustrates another embodiment of a reference card 360 for the prescriptions 202, 205, 208 of FIG. 2 using a common naming convention of graphical symbols. In this example, drug Tetracycline 220 may have the short name represented by a graphical symbol of a cat 362. Drug Lipitor 22 may have the short name represented by a graphical symbol of a dog 365, and drug Lisnopril 225 may have the short name represented by a graphical symbol of a horse 368. Similar to alphanumeric short names, short names using graphical symbols may be able to be selected, indicated, created and/or updated by a user such as a patient, an agent of the patient, a pharmaceutical professional and/or a system administrator. A default set of graphical symbols for short names may be available.

In FIG. 3c, the short names 362, 365, 368 may be mapped to be printed in sections 372, 375, 378, 380 of reference card 360 corresponding to their respective dosing regimes 228, 230, 232. In the example of FIG. 3c, the indications of the dosing regimes 332, 335, 338, 340 may use a graphical symbol representation, where the graphical symbol of a rooster 372 may correspond to morning, the graphical symbol of an analog clock showing 12:00 may correspond to noon, the graphical symbol of a moon and star may correspond to evening, and the graphical symbol of a bed may correspond to night. Other graphical symbols may be used, and may be able to be selected, indicated, created and/or updated by a user such as a patient, an agent of the patient, a pharmaceutical professional and/or a system administrator. For example, dosing regimes may be indicated per ingestion instructions (e.g., with water, with food, on an empty stomach) instead per times of ingestion, and a set of graphical representations of water, food, and empty stomach may be used. A default set of graphical symbols for indications of dosing regimes may be available.

Of course, if graphical symbols are used for indications of dosing regimes, other graphical symbols are not necessarily required to be used as the common naming convention for short names. Any common naming convention may be used in conjunction with any format or representation of indication(s) of dosing regimes.

FIG. 3c further illustrates an example of a vial 382 containing the medication for the Tetracycline prescription 202. The vial 382 may have a label 384 including standard labeling information, such as but not limited to an identification of the issuing medical professional, an Rx number, identification of the medication 386, a patient name, a dosing regime, and indication of refills, and the like. The label 384 may be printed and affixed to vial 382, or the labeling information 384 may be directly printed onto the vial 382. The identification of the vial contents or prescribed medicine 386 (in this example, Tetracycline 386) may be represented on label 384 using the same common naming convention 388 as used on its corresponding reference card 360. In this example, similar to the reference card 360, the graphical symbol of a cat 388 may be printed onto label 384. Although not illustrated, drug vials 382 for Lipitor 222 of prescription 205 and Lisnopril 225 of prescription 208 may have similarly printed labels on their corresponding vials 382. One of ordinary skill in the art will recognize that other types of drug containers may also be used in accordance with the present application, such as blister packs, medicament pouches, and other drug containers.

The common naming conventions shown in FIGS. 3a, 3b and 3c are exemplary. Many other common naming conventions may also be used, selected and updated as previously discussed. In a preferred embodiment, a common naming convention may be the same for each drug prescribed for a patient to aid in easier drug identification and remembrance, but other embodiments may have different common naming conventions for one or more different drugs prescribed for a patient.

Additionally, information printed onto the reference cards 302, 330, 360 is not limited to the illustrated short names and dosing regimes. Other pertinent information may also be printed onto cards 302, 330, 360 including, for instance, a patient name, drug names, pharmacy contact information, identification of issuing medical authority, and other such useful information.

In FIGS. 3a, 3b and 3c, reference cards 302, 330 and 360 are illustrated as stand-alone entities, however, they may be perforated from an information sheet that is distributed with a filled prescription or printed directly onto an information sheet itself. Short names using any format, printing characteristics and/or common naming conventions may also be printed or displayed on other vehicles other than reference cards 302, 330 and 360. A short name may be printed on, for instance, a medicament container or label thereon that is a receptacle for a filled prescription. A short name may be printed on a reusable label or other reminder mechanism so that a patient may distribute the short names and dosing regimes to multiple parties, e.g., multiple caregivers and/or medical professionals. A short name may be printed onto stocking labels for use in stocking medications at a filling entity. A short name may be displayed on a computer at a filling entity, on or with patient records, and the like. Other vehicles may display or have the short name printed thereon for the convenience of the patient or persons/entities associated with the patient.

Figure 4:
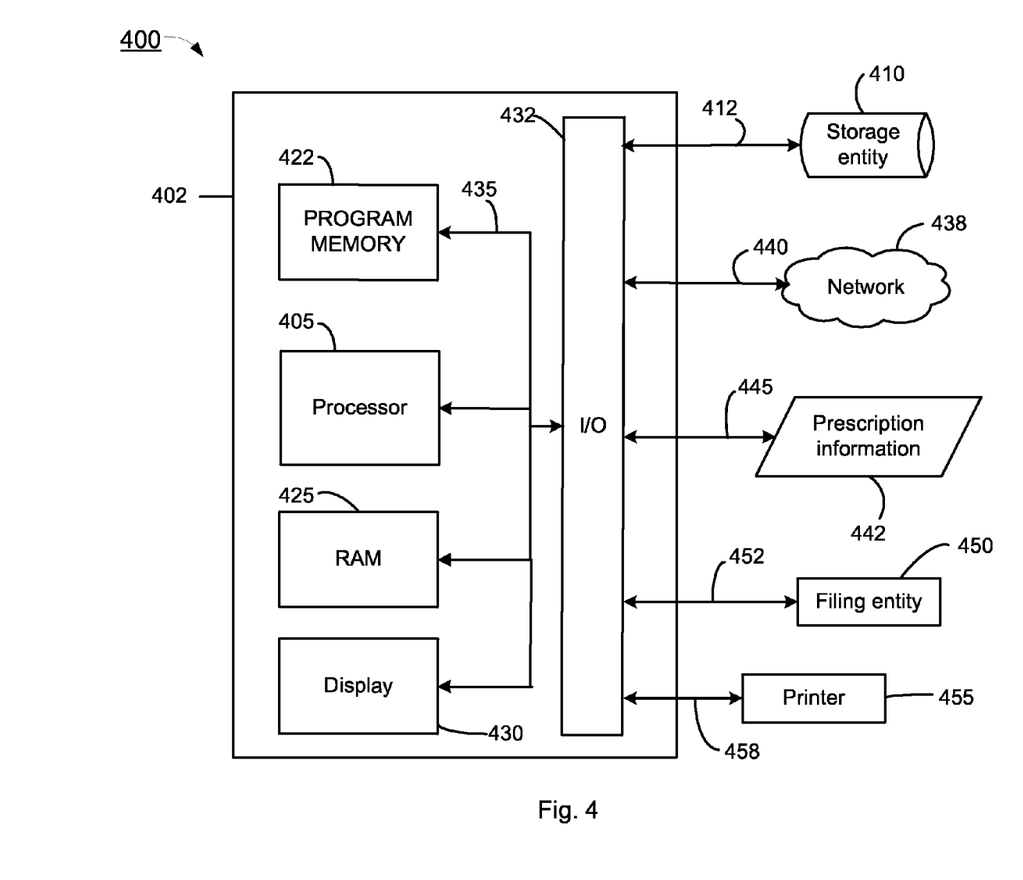
FIG. 4 depicts an embodiment of a system for coordinating and displaying a short name of a drug.

FIG. 4 depicts an embodiment of a system 400 for coordinating and displaying a short name of a drug. System 400 may operate in accordance with one or more embodiments of method 100 and other methods and embodiments thereof for coordinating, displaying and/or printing a short name of a drug. For the sake of illustration, a simplified block diagram of a computer 402 is used to illustrate the principles of the instant disclosure. However, such principles apply equally to other electronic devices, including, but not limited to, cellular telephones, personal digital assistants, media players, appliances, gaming systems, entertainment systems, set top boxes, and automotive dashboard electronics, to name a few. The computer 402 may have a processor 405 that is operatively connected to a database or storage entity 410 via a link 412. Link 412 may be as simple as a memory access function, or it may be a wired, wireless, or multi-stage connection through a network. Many types of links are know in the art of networking and are possible.

The storage entity 410 may be contained in the same entity as the computer 402, or it may be a separate local or remote entity. Storage entity 410 may be a database on a computer, server or other electronic device or it may be a storage device such as a hard drive, disk, mass storage device, or the like. Many types of storage entities are known in the art of data storage and may operate with the disclosure of this application. It should be noted that, while not shown, additional, multiple databases/storage entities may be linked to the computer 402 in a known manner. The storage entity 410 may include any data that may be relevant to coordinating, printing and displaying a short name for a drug, including but not limited to prescription information, drug names, dosing regimes, common naming conventions, user selected parameters and/or preferences, short names, patient records, etc. These and other types of relevant data relevant may be stored on a single storage entity 410 or across multiple storage entities 410.

Data stored in the storage entity 410 may be obtained by the computer 402 through a download, data transfer, or other such mechanism. Alternatively, the computer 402 may request or read the storage device 410 to obtain only the necessary data relevant to coordinating, printing and displaying a short name for a drug. Data may be entered into storage entity 410 by a user, at initialization or through a download, data transfer, or other such mechanism.

The computer 402 may include a processor 405 (may be called a microcontroller or a microprocessor) for executing computer executable instructions, a program memory 422 for permanently storing data related to the computer executable instructions, a random-access memory (RAM) 425 for temporarily storing data related to the computer executable instructions, a display 430 and an input/output (I/O) circuit 432, all of which may be interconnected via an address/data bus 435. It should be appreciated that although only one processor 405 is shown, the computer 402 may include multiple processors 405. Similarly, the memory of the computer 402 may include multiple RAMs 425 and multiple program memories 422. Although the I/O circuit 432 is shown as a single block, it should be appreciated that the I/O circuit 432 may include a number of different types of I/O circuits. The RAM(s) 425 and program memories 422 may be implemented as semiconductor memories, magnetically readable memories, and/or optically readable memories, for example.

The computer 402 may also be operatively connected to a network 438 via a link 440. Similar to link 412, the form of link 440 may take any form known in the art of networking. Information from the storage entity 410 may be accessed by computer 402 via link 440 and the network 438.

The computer 402 may receive prescription information 442 (such as from prescriptions 202, 205, 208 of FIG. 2) over a link 445. Link 445 may be the same entity as network link 440 or database link 412, or it may be a separate entity. Link 445 may be an operator/user interface, for example, via a touch screen display 430 or keyboard (not pictured) of computer 402, or it may be a local or remote network connection to a server, website, other computer, or a different database. The computer 402 may receive a plurality of prescription information 442 from a plurality of sources, for example, when a single computer 402 receives prescription information 442 from multiple medical entities such as doctors' offices, hospitals, and the like. In this case, multiple links 445 are possible.

The computer 402 may also be operatively connected to a filling entity 450 via a link 452. Link 452 may be the same entity as network link 440, database link 412 or prescription information link 445, or it may be a separate entity. Filling entity 450 may receive instructions from computer 402 and fill prescriptions according to the received instructions. Filling entities 450 may be automatic processes or systems, they may be manual or one or more physical persons, or some combination of the two. Multiple links 452 to multiple filling entities 450 may be possible. For example, a single computer 402 may host a website and receive a plurality of prescriptions for different patients from various locations across the country. The computer 402 may distribute filling instructions across multiple links 452 to multiple physical pharmacy store-fronts in proximity to the each patient's physical location, with each store-front having with its own filling entity 450. Another example may include linking to an automatic filling entity for one class of drugs, and linking to a manual filling entity for a different class of drugs. Other examples are also possible. Link 452 may be the same link as links 412, 440 or 445, or it may be a separate link. Link 452 may also be a local connection or a remote connection through network 438.

The computer 402 may also be operatively connected to a printer 455 via a link 458. Similar to link 412, the form of link 458 may take any form known in the art of networking. Information for printing may be sent by computer 402 via link 452 to printer 455. Information for printing may be sent by computer 402 via link 440 through network 438 to a printer 455, for instance, if the printer and the computer are not co-located. Other networking configurations are also possible.

Figure 5:
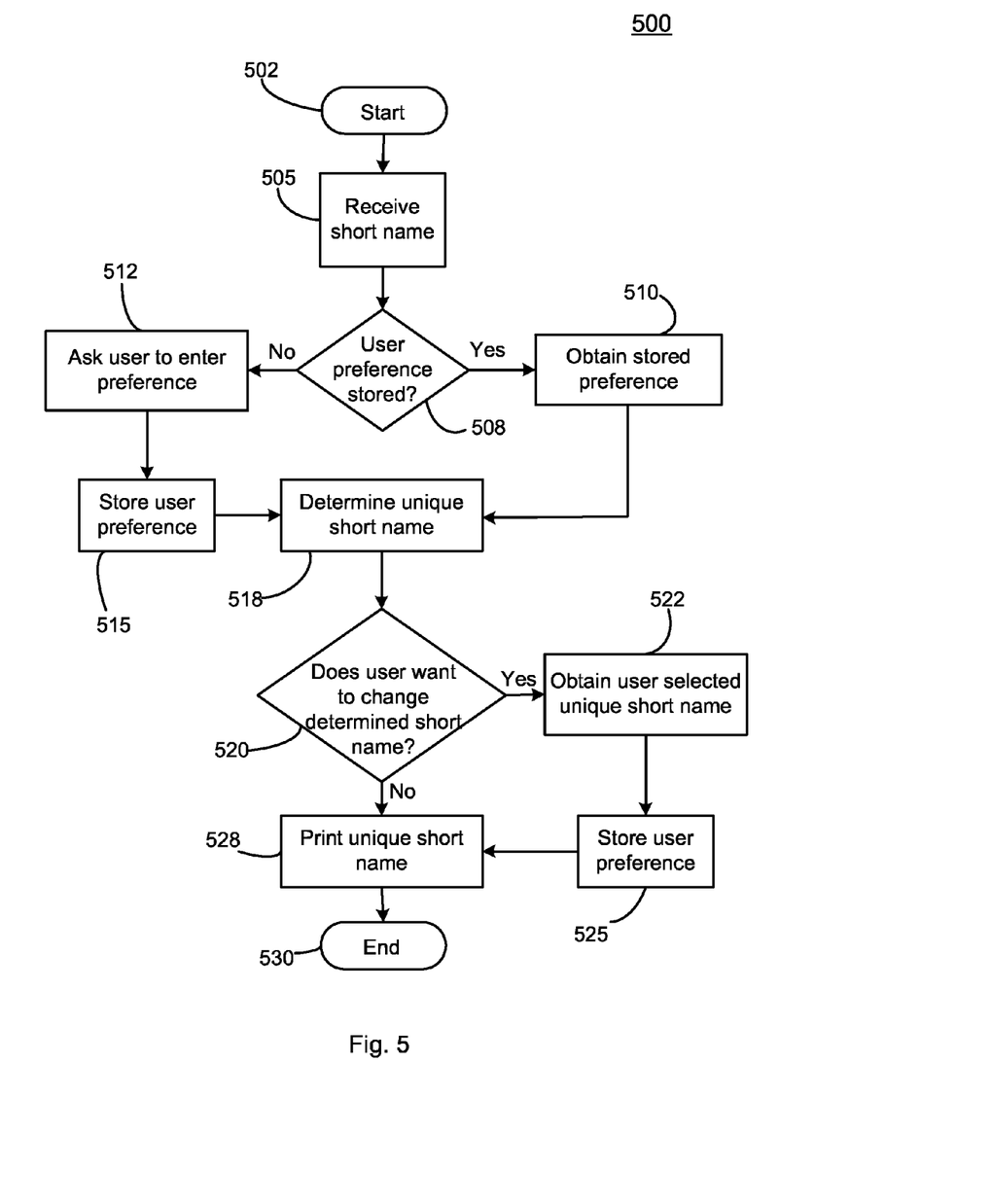
FIG. 5 shows an exemplary method of coordinating and printing a short name of a drug based on user input.

FIG. 5 illustrates an exemplary method 500 of coordinating and printing a short name of a drug based on user input. While the embodiment of method 500 shown in FIG. 5 is depicted for a single drug and its corresponding short name, method 500 may be extended to apply to multiple drugs prescribed to a patient. At the start (block 502), a short name may be received (block 505). The short name may be received (block 505) in a manner similar to, for instance, block 105 or block 108 of method 100. If a stored user preference is found at block 508, the stored user preference may be obtained (block 510). The stored user preference may indicate a preferred common naming convention, a preferred short name, or both. A "user," as used in FIG. 5, may be a patient, an agent of the patient, a pharmaceutical professional, or a system administrator for a system executing at least a part of an embodiment of method 500. If a stored user preference is not found at block 508, the user may be asked to enter a preference (block 512) and the entered preference may be stored (block 515). In some alternate embodiments, blocks 510 and 515 may be omitted.

Next, a determination of the short name is made (block 518). If a specific preferred short name has been stored by the user (such as from block 515 or 510), it may be retrieved to be the determination of the short name. Otherwise, the method 500 may determine the short name (block 518) based on a stored user-preferred common naming convention (such as from block 515 or block 510) or based on a default naming convention. A check may be made at block 520 to determine if the user agrees with the determined short name. This step may be omitted, for instance, if the user has recently entered a preferred short name, such as at block 510. If, at block 520, the user wants to change the determined short name, a user selected short name may be obtained (block 522) and stored (block 525). The short name may then be printed (block 528) and the method 500 may end (block 530).

If, at block 520, the user approves of the determined short name, then the short name may be printed (block 528) and the method 500 may end (block 520).

Method 500 and its embodiments may operate in accordance with an embodiment of method 100. Method 500 and its embodiments may operate in accordance with a system similar to system 400 of FIG. 4.

Although the forgoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

What is claimed:

1. A system of coordinating and displaying a short name for a drug, the system comprising a computer having computer-executable instructions for:
   receiving, from a patient or an agent of the patient, first user input for creating a common naming convention;
   storing the common naming convention so that the common naming convention is accessible to both (1) the patient or the agent of the patient, and (2) a pharmaceutical professional at a filling entity that performs at least one step in filling prescriptions, the filling entity including a computing device in communicative connection with the computer; and
   receiving, from the patient, the agent of the patient, or the pharmaceutical professional, second user input for creating a short name corresponding to a drug name, the drug name corresponding to a prescription for the patient for a drug, wherein:
      (i) the drug name is at least one of a brand name, generic name, or chemical name for the drug,
      (ii) the short name is based on the common naming convention,
      (iii) at least one of:
         a number of characters of the short name is less than a number of characters of the drug name, and the characters of the short name are nonnumeric, or
         the short name includes a graphical symbol; and
      (iv) the short name is unique across a set of short names corresponding to a set of prescriptions for the patient; and
   causing the short name to be presented at a user interface.

2. The system of claim 1, wherein:
   the short name is a first short name, the drug is a first drug, the drug name is a first drug name, the prescription is a first prescription, and the graphical symbol is a first graphical symbol; and
   the computer has further computer-executable instructions for:
      receiving, from the patient, the agent of the patient, or the pharmaceutical professional, third user input for creating a second short name corresponding to a second drug name, the second drug name corresponding to the first prescription or a second prescription for the patient for a second drug, wherein:
         the second drug name is at least one of a brand name, generic name, or chemical name for the second drug,
         the second short name is based on the common naming convention,
         at least one of:
            a number of characters of the second short name is less than a number of characters of the second drug name, and the characters of the second short name are non-numeric, or
            the second short name includes a second graphical symbol, and the second short name is unique across the set of short names corresponding to the set of prescriptions for the patient.

3. The system of claim 1, wherein the computer has further computer-executable instructions for receiving a selection of the common naming convention.

4. The system of claim 1, wherein the computer has further computer-executable instructions for causing the short name to be printed.

5. The system of claim 1, wherein the short name includes the graphical symbol.

6. The system of claim 1, wherein a set of characters of the short name is a subset of a set of characters of the drug name.

7. The system of claim 6, wherein the computer-executable instructions for causing the short name to be presented at the user interface comprise computer-executable instructions for causing the characters of the short name to be presented at the user interface within a set of characters of the drug name, the characters of the short name being presented in a different manner from a remainder of the characters of the drug name, the different manner including at least one of: capitalized, bold, italicized, a different color, a different case, a different size, or a different font.

8. The system of claim 1, wherein the user interface is one of: (i) a user interface that is accessible to the patient or to the agent of the patient, (ii) a user interface of the computer, (iii) a user interface of the computing device included in the filling entity, or (iv) another user interface or display.

9. The system of claim 1, wherein the computer has further computer-executable instructions for causing the short name to be presented at multiple user interfaces.

10. The system of claim 1, wherein the computer has further computer-executable instructions for updating at least one of the common naming convention or the short name.

11. The system of claim 10, wherein the at least one of the common naming convention or the short name is updated based on additional user input.

12. A system of coordinating and displaying a short name for a drug, the system comprising:
a processor;
a communicative link to a data storage device;
a communicative connection to a user interface accessible to a patient or to an agent of the patient;
a communicative connection to a computing device at a filling entity that performs at least one step in filling prescriptions; and
a set of computer-executable instructions stored on a memory that, when executed by the processor, cause the system to:
receive, from a patient or an agent of the patient, first user input for creating a common naming convention;
store, using the communicative link, the common naming convention in the data storage device so that the common naming convention is accessible to both (1) the patient or the agent of the patient, via the user interface accessible to the patient or to the agent of the patient, and (2) a pharmaceutical professional, via a user interface of the computing device at the filling entity;
receive, from the patient, the agent of the patient, or the pharmaceutical professional, second user input for creating a short name corresponding to a drug name, the drug name corresponding to a prescription for the patient for a drug, wherein:
(i) the drug name is at least one of a brand name, generic name, or chemical name for the drug,
(ii) the short name is based on the common naming convention,
(iii) at least one of:
a number of characters of the short name is less than a number of characters of the drug name, and the characters of the short name are nonnumeric, or
the short name includes a graphical symbol, and
(iv) the short name is unique across a set of short names corresponding to a set of prescriptions for the patient; and
store, using the communicative link, the short name in the data storage device.

13. The system of claim 12, wherein:
the short name is a first short name, the drug is a first drug, the drug name is a first drug name, the prescription is a first prescription, the graphical symbol is a first graphical symbol, and the set of computer-executable instructions is a first set of computer-executable instructions; and
the system further comprises a second set of computer-executable instructions that, when executed by the processor, cause the system to receive, from the patient, the agent of the patient, or the pharmaceutical professional, third user input for creating a second short name corresponding to a second drug name, the second drug name corresponding to the first or a second prescription for the patient for a second drug, wherein:
the second drug name is at least one of a brand name, generic name, or chemical name for the second drug,
the second short name is based on the common naming convention,
at least one of:
a number of characters of the second short name is less than a number of characters of the second drug name, and the characters of the second short name are non-numeric, or
the second short name includes a second graphical symbol, and
the second short name is unique across the set of short names corresponding to the set of prescriptions for the patient.

14. The system of claim 12, further comprising an additional set of computer-executable instructions that, when executed by the processor, cause the system to update, based on additional user input, at least one of the common naming convention or the short name.

15. The system of claim 12, wherein at least one of the common naming convention or the short name is selectable.

16. The system of claim 12, further comprising an additional set of computer-executable instructions that, when executed by the processor, cause the system to at least one of: (i) cause the short name to be printed, (ii) cause the short name to be presented at the user interface accessible to the patient or to the agent of the patient, (iii) cause the short name to be presented at the user interface of the computing device at the filling entity, or (iv) cause the short name to be presented at another user interface or display.

17. The system of claim 12, further comprising an additional set of computer-executable instructions that, when executed by the processor, cause the system to:
provide a default common naming convention; and
determine the short name based on default common naming convention when no indication of a selection of the common naming convention created by the patient or the agent of the patient is received.

18. The system of claim 12, wherein a set of characters of the short name is a subset of a set of characters of the drug name.

19. The system of claim 18, further comprising an additional set of computer-executable instructions that, when executed by the processor, cause the system to cause the short name to be presented at the user interface in a different manner than other characters presented at the user interface, the different manner including at least one of: capitalized, bold, italicized, a different color, a different case, a different size, or a different font.

20. The system of claim 12, wherein the common naming convention is a first common naming convention, and wherein the system further comprises additional computer-executable instructions that, when executed by the processor, cause the system to:

receive additional user input for creating a second common naming convention; and store the second common naming convention in the data storage device.

* * * * *